United States Patent
Schneeberger et al.

(10) Patent No.: US 8,167,581 B2
(45) Date of Patent: May 1, 2012

(54) DEVICE FOR DELIVERING A LIQUID, THE DEVICE COMPRISING A PUMP AND A VALVE

(75) Inventors: Niklaus Schneeberger, Pully (CH); Véronique Vallet, Bussigny-près-Lausanne (CH); Eric Chappel, Saint-Julien-en-Genevois (FR)

(73) Assignee: Debiotech SA, Lausanne (CH)

( * ) Notice: Subject to any disclaimer, the term of this patent is extended or adjusted under 35 U.S.C. 154(b) by 243 days.

(21) Appl. No.: 12/439,855

(22) PCT Filed: Sep. 3, 2007

(86) PCT No.: PCT/FR2007/051863
§ 371 (c)(1),
(2), (4) Date: Mar. 4, 2009

(87) PCT Pub. No.: WO2008/029051
PCT Pub. Date: Mar. 13, 2008

(65) Prior Publication Data
US 2010/0028170 A1   Feb. 4, 2010

(30) Foreign Application Priority Data
Sep. 4, 2006   (FR) ...................................... 06 53560

(51) Int. Cl.
F04B 49/10   (2006.01)
A61M 1/00   (2006.01)
(52) U.S. Cl. .......................... 417/278; 417/279; 604/153
(58) Field of Classification Search .................. 417/395, 417/472, 278, 279; 604/141, 247, 890.1, 604/891.1, 892.1, 151, 153, 65, 66, 67
See application file for complete search history.

(56) References Cited

U.S. PATENT DOCUMENTS

| | | | | |
|---|---|---|---|---|
| 4,299,220 A | * | 11/1981 | Dorman | 604/118 |
| 4,718,893 A | * | 1/1988 | Dorman et al. | 604/67 |
| 4,915,017 A | * | 4/1990 | Perlov | 92/5 R |
| 5,006,118 A | * | 4/1991 | Yule | 604/408 |
| 5,067,943 A | * | 11/1991 | Burke | 604/141 |
| 5,088,983 A | | 2/1992 | Burke | |
| 5,224,843 A | | 7/1993 | van Lintel | |
| 5,785,681 A | | 7/1998 | Indravudh | |
| 7,005,078 B2 | | 2/2006 | Van Lintel et al. | |
| 7,032,783 B1 | * | 4/2006 | Kamp et al. | 222/321.9 |
| 7,291,133 B1 | | 11/2007 | Kindler et al. | |

(Continued)

FOREIGN PATENT DOCUMENTS

EP   0420620 A2   4/1991
(Continued)

Primary Examiner — Devon C Kramer
Assistant Examiner — Bryan Lettman
(74) Attorney, Agent, or Firm — The Webb Law Firm

(57) ABSTRACT

A device for delivering a liquid including a pump, and an anti-siphon valve external to the pump is disclosed. The anti-siphon valve includes an inlet channel connected to the outlet duct of the pump, and an outlet channel, between which a seat and a moving member are disposed that are suitable for co-operating together and that define, between the inlet channel and the outlet channel, a leaktight liquid flow zone. The moving member is suitable for going from an opening position making it possible for liquid to flow through the flow zone, to a closure position in which the moving member comes into contact with the seat of the valve and prevents any flow through the flow zone, the moving member being subjected to the pressure of a reference chamber that is not in fluid communication with the outlet channel.

34 Claims, 3 Drawing Sheets

FOREIGN PATENT DOCUMENTS

| | | |
|---|---|---|
| EP | 0882466 A2 | 12/1998 |
| EP | 1283957 B1 | 10/2005 |
| WO | 9015929 A1 | 12/1990 |
| WO | 9532013 A1 | 11/1995 |

* cited by examiner

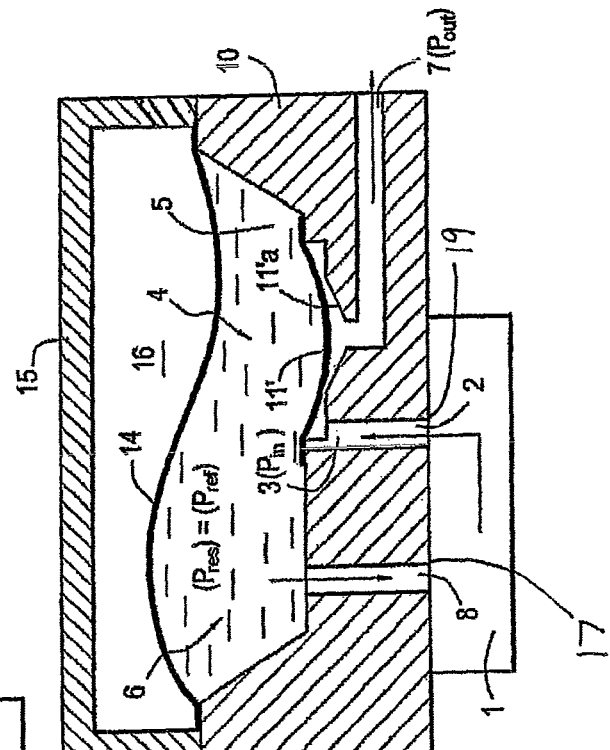
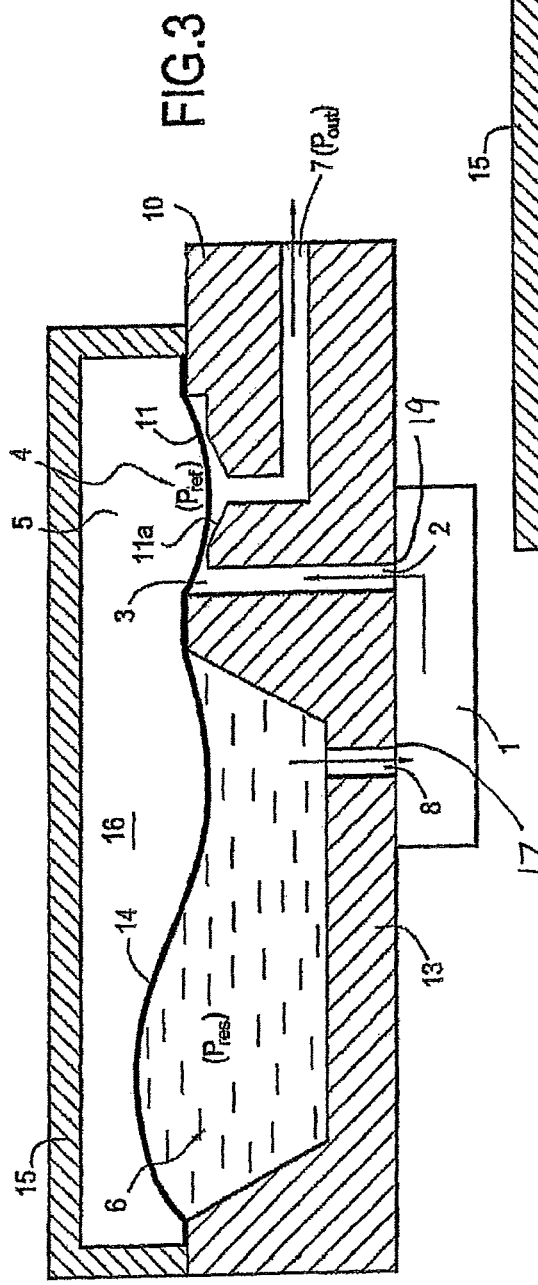

DEVICE FOR DELIVERING A LIQUID, THE DEVICE COMPRISING A PUMP AND A VALVE

The invention relates to a device for delivering a liquid, which device comprises a pump having an inlet duct suitable for being connected to a liquid reservoir and connected to an inlet control member of the pump, an outlet duct connected to an outlet control member of the pump, and a pumping portion having control means provided with a pumping membrane and a pumping chamber whose volume varies as a function of the deformation of the pumping membrane.

A siphoning effect represents a major problem for users of pumps for injecting liquid medication. If the pump or the liquid medication reservoir is situated at a height greater than the height of the place at which the injection is performed on the patient's body, the column of liquid in the injection line generates pressure that drives the liquid into the patient's body if the pump is not totally leaktight.

This situation often occurs for ambulatory injection pumps in which the pump contains the liquid medication reservoir, such as insulin pumps of the Continuous Subcutaneous Infusion of Insulin (CSII) type.

If one of the technical characteristics of the injection pump is that it uses a liquid medication reservoir that is of variable volume, a similar danger can occur when the reservoir is subjected to pressure. If the reservoir is situated inside a ventilated housing, as applies in pumps of the CSII type, and the ventilation system fails, such a pressure can occur.

In everyday life, that situation can occur if a user of such a type of pump goes swimming in the sea or in a swimming pool with that pump. When the patient comes out of the water, the membrane of the hydrophilic filter that protects the ventilation system from intake of water becomes blocked with salt coming from the seawater drying, and, in this situation, the air pressure at sea level of about 100 kilopascals (kPa) becomes trapped inside the housing. Subsequently, if the user is on board an airplane that climbs rapidly to its cruising altitude, at which the passenger compartment presents a predetermined pressure of about 72 kPa that is less than the value of the pressure at sea level, the pressure that is trapped inside the housing generates a thrust of 28 kPa driving the liquid medication from the reservoir towards the patient.

In an alternative situation in everyday life, a patient can place the pump at a level that is higher than the injection site. Depending on the length of the injection line and on the above-mentioned difference in level, suction is generated at the outlet of the pump by the siphon effect, due to the weight of the liquid. In this situation too, the liquid medication is driven by the pressure difference (or "siphon pressure" $P_{siph}$) towards the patient. In a typical situation, with an injection line that has a length of 1 meter (m) and with the medication having a density that is close to the density of water, said pressure differences can be as high as 10 kPa.

All of those situations present a danger due to a common factor that is the positive pressure difference (or "extra pressure") between the liquid medication reservoir and the place of injection on the patient's body.

Usually, in order to mitigate that risk, "crack valves" are used in the zone in which the liquid flows, those valves being closed by default and opening at pressures greater than the maximum pressure difference that can be expected (EP 0 882 466). Unfortunately, for each injection, the pump must overcome the barrier set up by the crack valve. That solution thus suffers from the drawback of increasing the pressure required for performing the injection. That increase in injection pressure gives rise to degradation in the quantity of energy consumed and in the precision of the doses metered out by the pump. In addition, pressure differences between the reservoir and the outlet of the pump that are larger than those normally expected, can open the valve. Dimensioning of the valve is therefore critical.

In pumps of the positive displacement type (e.g. as in WO 90/15929 and in EP 183 957), it is possible to use an Anti-Siphon Valve (ASV) having three ports as an outlet control member of the pump itself. Such an anti-siphon valve (see 18 in FIG. 1 of WO 90/15929) is an integral part of the pump and it has an inlet channel 20 and an outlet channel 3 for the liquid and a reference port (reference pressure $P_{ref}$ that is the external pressure above the moving membrane 18a). No liquid flow is possible from the reference port towards the outlet through such a valve. The liquid flow zone between the inlet and the outlet opens or closes firstly as a function of the pressure differences between the inlet port $P_{in}$ and the reference port $P_{ref}$ and between the reference port $P_{ref}$ and the outlet $P_{out}$.

Depending on the dimensioning of said anti-siphon valves, the two pressure differences $\Delta P_{in} = P_{in} - P_{ref}$ and $\Delta P_{out} = P_{ref} - P_{out}$ act simultaneously on the anti-siphon valve but can have different magnitudes for opening the flow zone, as is shown diagrammatically in FIG. 1. In this diagram, a valve state that is characterized by the two pressure differences $\Delta P_{in}$ and $\Delta P_{out}$ is represented by a point with the co-ordinates ($\Delta P_{in}$, $\Delta P_{out}$). If that point is situated the hatched zone, the valve is closed, and if the point is situated in the non-hatched zone, the valve is open. The curve that separates the two zones represents the transition between open and closed, and it is thus characteristic for the valve.

In order to explain how anti-siphon valves operate, firstly consideration is given below to the situation in which the inlet pressure is in equilibrium with the reference pressure and $\Delta P_{in}$ is thus equal to zero. This particular situation corresponds to the horizontal axis of FIG. 1. When the pressure difference $\Delta P_{out}$ is greater than $T_{out}$ (outlet pressure threshold), which is a set value that is intrinsic to the anti-siphon valve, then the anti-siphon valve is closed (hatched zone of FIG. 1). Conversely, when the pressure difference $\Delta P_{out}$ is less than $T_{out}$, then the anti-siphon valve is open (non-hatched zone in FIG. 1).

In another particular situation that corresponds to the vertical axis, if the reference pressure is in equilibrium with the outlet pressure and $\Delta P_{out}$ is thus equal to zero, the valve opens when the pressure difference $\Delta P_{in}$ is greater than $T_{in}$ (inlet pressure threshold), which is another set value that is intrinsic to the anti-siphon valve.

It is thus either when $\Delta P_{in}$ increases, or when $\Delta P_{out}$ decreases (or when both occur at the same time) that the anti-siphon valve goes from the closed position to the open position, and vice versa.

The curve that is representative of the opening and closure principle for opening and closure of such anti-siphon valves can be described as the function $f(\Delta P_{out})$, and it can be understood that the valve is open under the conditions ($\Delta P_{in}$, $\Delta P_{out}$) if $\Delta P_{in} > f(\Delta P_{out})$. It can also be understood that the pressure thresholds $T_{out}$ and $T_{in}$ are point of intersection of that function with the axes.

FIG. 2 is a more general example of a curve representative of the opening and closing principle for opening and closure of such anti-siphon valves, for a representation that is not rectilinear as in FIG. 1 (where $f(\Delta P_{out} = T_{in} + \Delta P_{out} (T_{in}/T_{out}))$, but that presents another shape satisfying the general principle of an $f(\Delta P_{out})$ relationship.

In all of the cases of curves representing the $f(\Delta P_{out})$ relationship, regardless of the starting point ($\Delta P_{in}$, $\Delta P_{out}$) representing a given situation of the valve:

starting from a location situated in the open zone (non-hatched zone situated on the left of the curve), and if provision is made to cause $\Delta P_{in}$ to decrease, then, as soon as $\Delta P_{in}$ reaches or remains below $f(\Delta P_{out})$ ($T_{in}$ if on the y-axis), the pressure threshold being crossed in this way causes the valve to close;

starting from a location situated in the open zone, and if provision is made to cause $\Delta P_{out}$ to increase, then, as soon as $\Delta P_{out}$ reaches or remains above x, where x is the solution of the equation $\Delta P_{in}=f(x)$, the pressure threshold being crossed in this way causes the valve to close;

starting from a location situated in the closed zone (hatched zone situated on the right of the curve), and if provision is made to cause $\Delta P_{in}$ to increase, then, as soon as $\Delta P_{in}$ reaches or remains above $f(\Delta P_{out})$ ($T_{in}$ if on the x-axis), the pressure threshold being crossed in this way causes the valve to open; and starting from a location situated in the closed zone, and if provision is made to cause $\Delta P_{out}$ to decrease, then, as soon as $\Delta P_{out}$ reaches or remains below x, where x is the solution $\Delta P_{in}=f(x)$, the pressure threshold being crossed in this way causes the valve to open.

Such anti-siphon valves, whose opening and closure principle is shown in FIGS. 1 and 2, present an inlet threshold $T_{in}$ of positive value and an outlet threshold $T_{out}$ of negative value, so that the point O (origin where $\Delta P_{in}=\Delta P_{out}=0$) is situated in the closed zone: it is then said the valve is closed by default.

In an ideal configuration, the pressure $P_{ret}$ of the reference port or of the reference chamber is in equilibrium with the pressure of the liquid in the liquid medication reservoir $P_{res}$, i.e. $P_{res}=P_{ref}$, and the valve opens only for pressure differences that are sufficiently small $\Delta P_{out}=P_{res}-P_{out}$. In this ideal configuration, the additional pressure differences between the liquid reservoir $P_{res}$ and the outlet of the injection pump enable the anti-siphon valve (ASV) to close, either due to the arrangement of the pressures inside the pump or else due to a column of liquid sucking the liquid from the outlet of the pump.

In such systems (described, for example, in WO 90/15929 and in EP 183 957) in which the anti-siphon valve is placed at the outlet of the pump as an outlet control member of the pump itself, provision is made so that $P_{res}=P_{ref}$. In the above-described disaster scenario, if the salt coming from the swimming water blocks the ventilation of the housing containing the pump, the air pressure at sea level of about 100 kPa becomes trapped inside the housing as reference pressure $P_{ref}$ so that, when the user is inside an airplane passenger compartment in which the pressure is 72 kPa, the extra pressure of 28 kPa causes the inlet control member (valve 16 in FIG. 1 of WO 90/15929) to open, and the pressure inside the reservoir of 100 kPa comes into equilibrium with the pressure at the inlet of the anti-siphon valve (zone 20 in FIG. 1 of WO 90/15929) and the following situation is reached: $P_{in}=P_{res}=P_{ref}$ and therefore $\Delta P_{in}=0$ and $\Delta P_{out}=28$ kPa. Thus, the anti-siphon valve does indeed close if $T_{out}<28$ kPa. If, for any reason, the pressure difference $\Delta P_{out}$ is even greater than 28 kPa, the anti-siphon valve remains closed and thus performs its safety function.

This is the opposite of what happens in a valve for which an additional pressure difference makes it possible to open the valve and an additional negative pressure difference makes it possible to close the valve.

Therefore, such an anti-siphon valve can be designed with a start-of-flow pressure (or "outlet pressure threshold") $T_{out}$ that is smaller than the expected pressure differences and thus that is smaller than the start-of-flow pressure (or "inlet pressure threshold") $T_{in}$ of a simple two-port valve.

Micropumps, such as those used in EP 183 957, present advantages for injecting liquid medication, including the advantages of having high precision and small pumping volume. Using micro-machining technology, it is also possible to fabricate micropumps that have a compression ratio that is sufficiently high for them to be self-priming, in spite of their small pumping volume. This is obtained by reducing all of the volumes in the pump proportionally to the pumping volume. Unfortunately, in micro-machining, the valves are made of hard materials (e.g. silicon) because it is not possible to incorporate soft materials into micro-machining methods, in particular for the moving portion and/or the seat of the valve.

Therefore, that type of pump is extremely sensitive to dust and to particles that can lodge themselves between the contact surfaces of the valve that are made of hard materials, thereby preventing any possibility of leaktight closure. Non-leaktight valves make dangerous leaks possible if there is a pressure difference between the liquid medication reservoir and the place of injection.

For example, in the above-discussed disaster situation, even though the pressure difference $\Delta P_{out}=28$ kPa causes the valve to close, if there are leaks due to particles, that pressure difference nevertheless drives the liquid towards the patient, and the safety function is not guaranteed.

An object of the present invention, is to provide a device that makes it possible to overcome the drawbacks of the prior art, and in particular that offers the possibility of combining the advantages of self-priming micropumps with the advantages of anti-siphon valves that are less sensitive to particles.

To this end, according to the present invention, the above-presented device for delivering a liquid is characterized in that it further comprises an anti-siphon valve external to the pump and having an inlet channel connected to the outlet duct of the pump, and an outlet channel, between which channels a seat and a moving member are disposed that are suitable for co-operating together and that define, between the inlet channel and the outlet channel of the valve, a leaktight liquid flow zone, said moving member being suitable for going from an opening position making it possible for liquid to flow through said flow zone, to a closure position in which the moving member comes into contact with the seat of the valve and prevents any flow through said flow zone, said moving member being subjected to the pressure of a reference chamber that is not in fluid communication with the outlet channel.

In this way, it can be understood that, by combining a micropump with an external valve, it is possible to maintain the precision of the micropump while broadening the range of possible valve types that can be used.

An anti-siphon valve that is external to the pump can advantageously be obtained using techniques different from micro-machining techniques, and thus, for example, for forming anti-siphon valves of the macroscopic type that are less sensitive to particles.

In a preferred feature, the seat and/or the moving member of said anti-siphon valve is made of a soft material, e.g. of elastomer, in particular of silicone or of natural rubber, or indeed of synthetic rubber.

In this manner, by using a soft external valve, it is possible to maintain the precision of the micropump and the tolerance to particles is improved, and thus the risks of the valve leaking in the closed position are reduced compared with such risks in a valve in which the closure contact zones are made of hard materials (e.g. materials used for manufacture by micro-machining techniques, such as silicon, metal oxides, etc.).

Thus, in this way, it is possible to combine the advantages of a pump of small size that can be micro-machined with the advantages of soft valves that are tolerant to particles.

In practice, such an external valve presents a size that is larger than the size of a micro-machined valve, and thus also dead volume that is larger. During the self-priming, the micropump must compress the gas throughout said volume until the opening threshold $T_{in}$ of the external valve is reached in order for said gas to penetrate into said valve and cause the liquid to advance. The dead volume and the opening threshold (or inlet pressure threshold) $T_{in}$ of said external valve thus influence the self-priming properties of the micropump and thus of the entire system.

Preferably, the moving member of the anti-siphon valve is caused to go between its closure position and its opening position at least by the pressure ($P_{ref}$) prevailing in the reference chamber.

In fact, the moving member of the anti-siphon valve is caused to open by two pressure differences, namely $\Delta P_{in}=P_{in}-P_{ref}$ and $\Delta P_{out}=P_{ref}-P_{out}$.

In a preferred particular embodiment, the external valve is open by default, and thus the predetermined outlet pressure threshold $T_{out}$ is positive and the predetermined inlet pressure threshold $T_{in}$ is negative. This preferred embodiment is shown in FIGS. 5 and 6. The moving member is in the opening position when said valve is in the equilibrium position in which the pressures in the inlet channel ($P_{in}$), in the outlet channel ($P_{out}$), and in the reference chamber ($P_{ref}$) are mutually equal. In addition, the moving member goes into its closure position, from said equilibrium position of the anti-siphon valve, if the pressure in the outlet channel ($P_{out}$) decreases at least by the value of a predetermined outlet pressure threshold ($T_{out}$), the pressures in the inlet channel ($P_{in}$) and in the reference chamber ($P_{ref}$) remaining constant. Also, the moving member goes into its closure position, from said equilibrium position of the anti-siphon valve, if the pressure in the reference chamber ($P_{ref}$) increases at least by the absolute value of a predetermined inlet pressure threshold ($T_{in}$), the pressures in the outlet channel ($P_{out}$) and in the reference chamber ($P_{ref}$) remaining constant.

In which case, the self-priming capacity of the micropump is no longer affected by the external anti-siphon valve because it is not necessary to compress the gas at the outlet of the of pump in order to exceed the inlet pressure threshold $S_{in}$ and cause the gas to enter the anti-siphon valve.

In another preferred feature, the pump is a micropump, i.e. a micro-mechanical pump manufactured by micro-machining techniques.

If said outlet channel of the anti-siphon valve is connected to an injection line (which, for example, is terminated by a injection catheter), advantageously said predetermined closure pressure threshold ($T_{out}$) is less than the inverse of the siphon pressure ($-P_{siph}$) prevailing in the valve, if said injection line is disposed vertically with the distal end (the end that is close to the patient) downwards.

In which case, this means that the following inequality is satisfied:

$$0<T_{out}<-P_{siph}=L\times G\times D$$

where L is the length of the injection line, G is the gravitational constant, and D is the density of the fluid.

In another feature of the present invention, said reference pressure ($P_{ref}$) is substantially equal to the pressure prevailing in the inlet duct of the pump, when the pump is at rest (inactive) or in the equilibrium state.

As regards, in particular, the structure of the device, one or more of the following features can be implemented:

said valve presents a valve body in which said inlet channel, said flow zone, and the outlet channel are formed;

said moving member belongs to a flexible film that is fastened in leaktight manner to the surface of the valve body, and that extends along said flow zone; preferably said film is made of an elastic material or of combinations (such as superposed layers) of polymers such as polyvinyl chloride, polyethylene, polycarbonate, polyamide, or a polyolefin, and in particular an elastomer polymer such as silicone, polybutadiene, synthetic rubber of the Viton (registered trademark) type, ethylene-propylene rubber, or natural rubber;

said reference chamber is in communication with the inlet duct of the pump;

the device further comprises a liquid reservoir connected to said inlet duct of the pump;

the reference chamber is subjected to the same pressure ($P_{ref}$) as the pressure ($P_{res}$) prevailing in the liquid reservoir;

said liquid reservoir presents a variable volume; in particular, said liquid reservoir comprises a stationary reservoir body and a moving reservoir wall defining the cavity of said liquid reservoir; in which case, preferably, said moving reservoir wall is fastened in leaktight manner to the outside surface of the stationary reservoir body; and/or said moving reservoir wall is formed of a flexible film that is preferably made of polymer material or of combinations such as superposed layers) of polymer materials such as polyvinyl chloride, polyethylene, polycarbonate, polyamide, or a polyolefin, or in particular an elastomer polymer such as silicone, polybutadiene, synthetic rubber of the Viton (registered trademark) type, ethylene-propylene rubber, or natural rubber;

the pressure ($P_{res}$) prevailing in said liquid reservoir is substantially equal to the pressure prevailing outside the liquid reservoir; in which case, preferably said stationary valve body and said stationary reservoir body are formed in a single piece forming a stationary body; and in particular said valve and said liquid reservoir are defined by the same surface of said stationary body forming the valve body and the reservoir body;

the flexible film of the moving member and the flexible film of said moving reservoir wall are made of the same flexible film; in particular, said single flexible film comprises a flexible first layer and a soft second layer that is situated on that face of the film that faces towards the reservoir and towards the seat of the anti-siphon valve; in particular, said single flexible film is fastened against said surface of the single stationary body in leaktight manner so as to form said flow zone of said anti-siphon valve and the cavity of said liquid reservoir; for example, said flexible film is fastened in leaktight manner against said stationary body by ultrasound welding, by heat-sealing, by laser welding, by adhesive bonding, by a technique of precision fitting under pressure, or indeed by a retaining technique, such as by using a clip, or by hot clamping;

said liquid reservoir further comprises a cover mounted on said stationary reservoir body, said moving reservoir wall being received between said cover and said stationary reservoir body; in particular, said reference chamber is connected to the space defined between the cover and the moving reservoir wall; and/or said cover is mounted on said stationary body forming said stationary valve body and said stationary reservoir body said cover and said stationary body defining a space that encloses said liquid reservoir and said reference chamber;

said pump is a pump of the positive displacement type;

said pump is self-priming in the absence of the anti-siphon valve, i.e. said pump has a compression ratio that is higher than the ratio of the absolute opening pressures of the inlet and the outlet valves (the compression ratio being defined as the ratio of the pumping volume to the sum of the pumping volume and of the internal dead volume between the two control members);

the pump has a small pumping volume that is smaller than 10 microliters (µl), preferably smaller than 1 µl, and preferably smaller than 500 nanoliters (nl); in particular, the pump is manufactured using micro-machining techniques.

Other advantages and characteristics of the invention appear on reading the following description given by way of example and with reference to the accompanying drawings, in which:

FIGS. 1 and 2 (described above) diagrammatically show the opening and closure principle for opening and closure of an anti-siphon valve;

FIG. 3 is a diagrammatic section view of a first embodiment of a device of the invention;

FIG. 4 is a diagrammatic section view of a second embodiment of a device of the invention.

Figure 1:
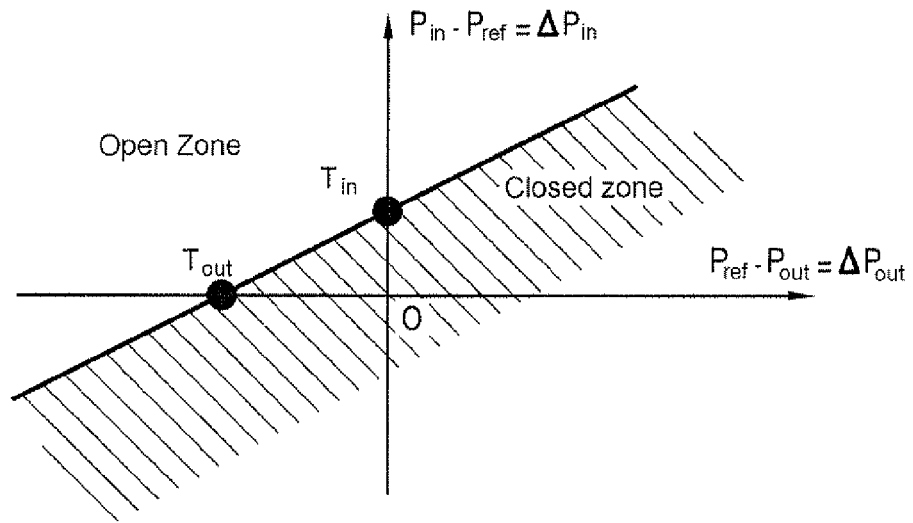

In the first and second embodiments that are described below, the device of the invention can include a pump 1 of the self-priming micro-mechanical pump or micropump type as presented in Document EP 739 451 that is made essentially of silicon and of glass.

In FIGS. 3 and 4, this micropump 1 is shown diagrammatically in the form of a box, but, among its components, it includes:

a liquid inlet control member or inlet valve 17 and a liquid outlet control member or outlet valve 17 (which members are not shown);

an inlet duct 8 connected to the inlet control member 17 of the pump 1, in which member 17 is situated downstream from the inlet duct 8;

an outlet duct 2 connected to the outlet control member 19 of the pump 1, which member 19 is situated upstream from the outlet duct 2; and a pumping portion (not shown) comprising control means provided with a pumping membrane and a pumping chamber whose volume varies as a function of the deformation of the pumping membrane.

A pump 1 is chosen that has a compression ratio that is sufficiently high to exceed the opening pressure of the internal valves serving as liquid inlet and outlet control members 17, 19 for a compressible fluid such as air.

The inlet duct 8 is suitable for being connected to a liquid reservoir 6 which, in the embodiment shown, is an integral part of the device, but which could be in a separable form.

The device also includes an external anti-siphon valve 4 that is separate from the pump 1. The inlet channel 3 of the valve 4 is connected to the outlet duct 2 of the pump 1.

A valve 4 is chosen in which both of or at least one of the elements constituted by the moving portion 11 and by the seat 11a that faces said moving portion are/is made of a soft material. In this way, the anti-siphon valve 4 remains leaktight in its closure position in spite of the presence of dust and of particles.

The term "soft material" is used to mean a material that is not rigid, and whose type and/or thickness make(s) the moving portion 11 elastic and/or pliable so as to deform and absorb variations in surface states due to the presence of dust and of particles, of size of the order of in the range a fraction of one micrometer to a few micrometers.

For example, said soft material is an elastomer polymer such as silicone, polybutadiene, synthetic rubber of the Viton (registered trademark) type, ethylene-propylene rubber, or natural rubber.

In the example shown, the moving portion 11 is a flexible film of polymer such as polyvinyl chloride, polyethylene, polycarbonate, polyamide, or polyolefin, having a thickness lying in the range 5 micrometers to 200 micrometers.

In the example shown, the valve 4 is formed in a housing 10, e.g. made of a rigid plastics material, in which the following are formed:

the inlet channel 3 of the valve 4 that is connected to the outlet duct 2 of the pump 1;

the outlet channel 7 of the valve 4 that is mounted on the upstream end of the injection line (not shown), whose downstream end is connected to the patient, e.g. at a catheter; and the seat 11a of the valve that is situated between the inlet channel 3 and the outlet channel 7, and in fluid communication with said channels.

The film constituting the moving member 11 is fastened in leaktight manner to the surface of the valve body 10, all around the seat 11a of the valve 4.

By means of the moving member 11, the inlet channel 3, the outlet channel 7, and the seat 11a of the valve define a leaktight liquid flow zone that is situated downstream from the pump 1 and upstream from the patient (not shown).

That face of the moving portion 11 that faces away from the seat 11a is in contact with a reference chamber 5 whose pressure $P_{ref}$ influences the position (open or closed) of the valve 4, as a function of the value of the pressure $P_{out}$ prevailing in the outlet channel 7 of the valve 4.

In the example shown, the reservoir 6 has been formed in a reservoir body 13 defining a cavity that can be filled with the liquid medication, which cavity is closed by a reservoir wall 14. In this example, the reservoir wall 14 is a moving wall and is formed of a flexible film of polymer, fastened in leaktight manner to the surface of the reservoir body 13.

The reservoir 6 is designed to be filled with liquid, without any gas being present in order to avoid any risk of gas arriving in the pump 1. In order to enable the volume of the reservoir 6 to vary while it is being filled or while it is emptying, the moving reservoir wall 14 is formed by a film that can deform (a flexible film) without it being elastic or extensible. To this end, it is possible to use a polymer such as polyvinyl chloride, polyethylene, polycarbonate, polyamide, or polyolefin, of a thickness lying in the range 5 micrometers to 200 micrometers.

For reasons of simplicity, as can be seen in FIG. 3, the housing 10 of the valve 4 and the reservoir body 13 form two portions of the same piece forming a stationary body 10/13 for the device, and it is a single film 11/14 that constitutes the moving reservoir wall 14 and the moving member 11 of the valve 4.

For this single film 11/14, it is possible to choose a flexible film made of a material such as those presented above. It is also possible to provide a film 11/14 formed of a superposition of at least two layers, namely:

a first layer that is flexible and that can be made of a material such as those presented above in order to be incapable of spreading; and a second layer that is soft, that is situated on that face of the film 11/14 that faces towards the reservoir 6 and towards the seat 11a of the valve 4, and that is, for example, made of an elastomer polymer such as silicone, polybutadiene, synthetic rubber of the Viton (registered trademark) type, ethylene-propylene rubber, or natural rubber.

A cover 15 overlies the stationary body 10/13 while extending above the reservoir 6 and the valve 4, the pump 1 being situated on another face of the stationary body 10/13.

The cover 15 is not mounted in leaktight manner on the stationary body 10/13 but it should prevent any liquid from entering the device, in particular into the cavity 16 of the cover 15. To this end, ventilation (not shown) is provided between the outside of the cover 15 and the cavity 16 of the cover 15, with a hydrophobic filter.

Thus, it can be understood that the external air pressure (external pressure) outside the device (outside the cover 15) can penetrate into the cavity 16 of the cover 15. In this way, by means of the flexibility of the film constituting the moving reservoir wall 14 and the moving member 11 of the valve 4, said external pressure is also the pressure that is exerted inside the reservoir 6 (liquid pressure $P_{res}$) and inside the reference chamber 5 (gas pressure $P_{ref}$) of the valve 4.

By means of the configuration presented above, the (gas) pressure $P_{ref}$ of the reference chamber 5 is thus the same as the liquid pressure ($P_{res}$) prevailing in the liquid medication reservoir 6.

Figure 5:
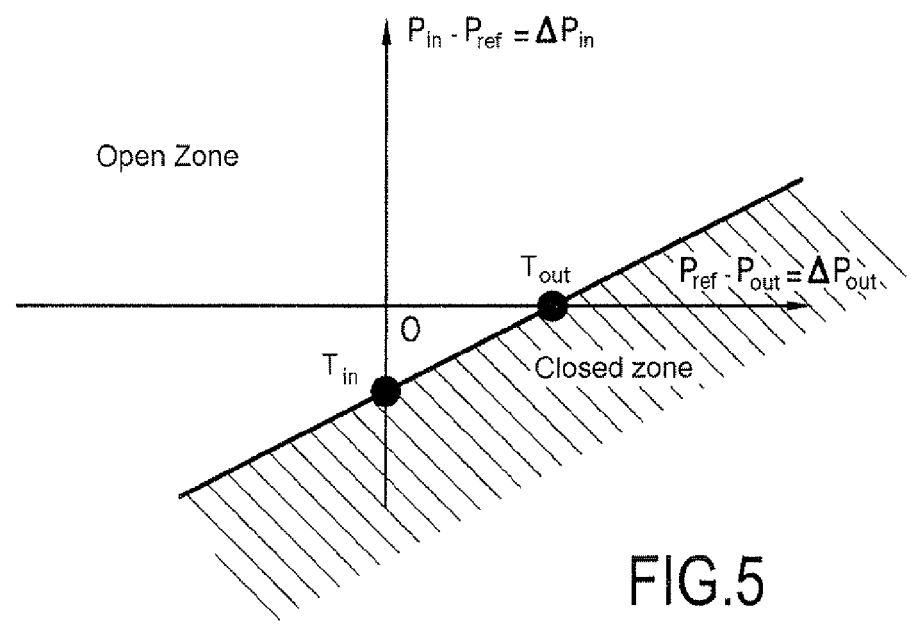
FIGS. 5 and 6 are diagrams showing the opening and closure principle for opening and closure of an anti-siphon valve in a preferred particular embodiment in which the external valve is open by default.
Figure 2:
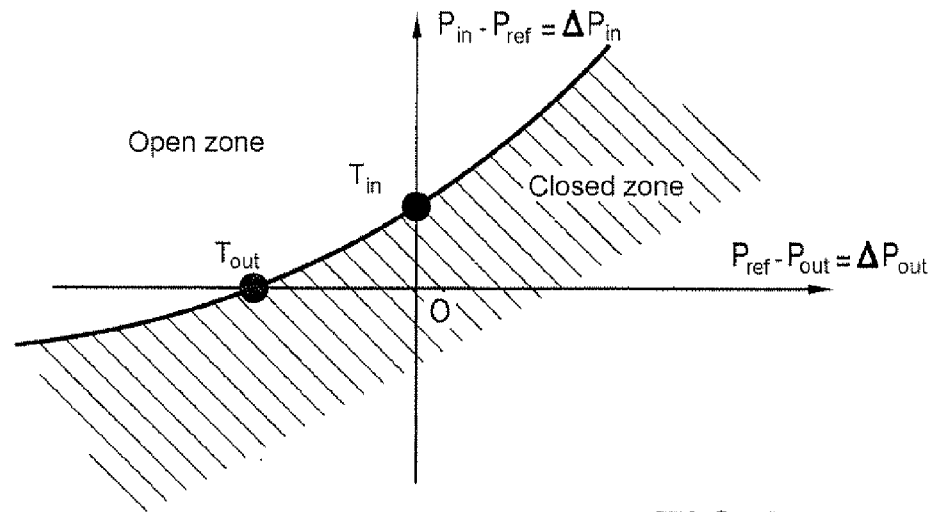
Figure 6:
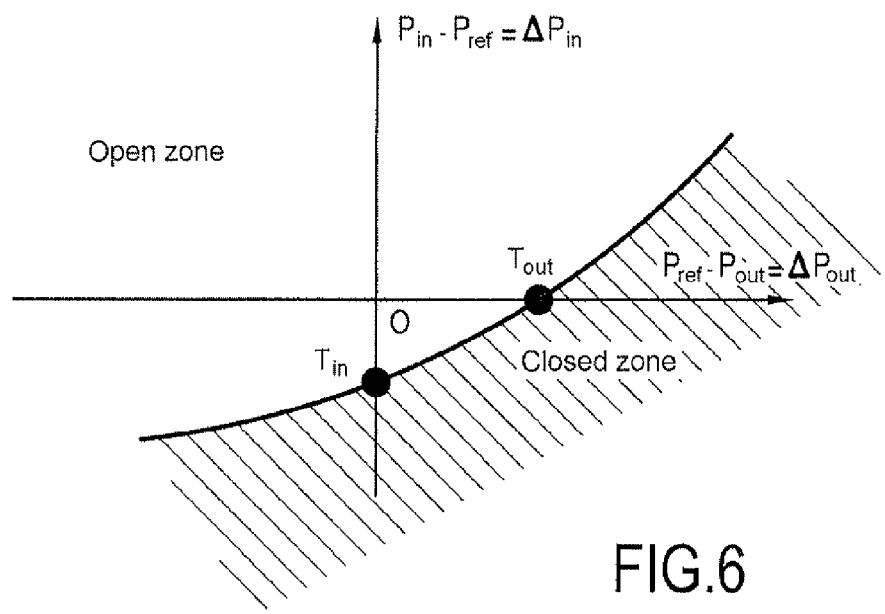

A preferred particular embodiment in which the external valve is open by default is shown in its operating mode in FIGS. 5 and 6 (the physical structure can be the physical structure of the first embodiment shown in FIG. 3, or the physical structure of the second embodiment shown in FIG. 4).

The valve 4 then has an outlet pressure threshold $T_{out}$ that is positive, i.e. it is open if the pressure $P_{out}$ prevailing in the outlet channel 7 of the valve 4 is equal to or greater than the pressure $P_{ref}$ prevailing in the reference chamber 5 minus the outlet pressure threshold $T_{out}$ of the valve 4 ($P_{out} \geq P_{ref} - T_{out}$), when the inlet pressure $P_{in}$ is in equilibrium with the reference pressure $P_{ref}$.

Conversely, i.e. when the pressure $P_{out}$ prevailing in the outlet channel 7 of the valve 4 is less than the pressure $P_{ref}$ prevailing in the reference chamber 5 by a certain difference (outlet pressure threshold $T_{out}$ of the valve 4), or $P_{out} < P_{ref} - T_{out}$, and when the inlet pressure $P_{in}$ is in equilibrium with the reference pressure $P_{ref}$, the valve is in the closed position.

In this preferred particular embodiment, the valve 4 presents an inlet pressure threshold $T_{in}$ of negative value: when the outlet pressure $P_{out}$ is in equilibrium with the reference pressure $P_{ref}$, then the valve is open if $\Delta P_{in} \geq T_{in}$, and the valve is closed if $\Delta P_{in} < T_{in}$.

In this particular situation, in which the anti-siphon valve is open in the equilibrium position, as shown in FIGS. 5 and 6 (the origin O, where $\Delta P_{in} = \Delta P_{out} = 0$, is situated in the open zone), it can be understood that the dead volume of the anti-siphon valve does not have any impact on the self-priming performance of the micropump, because it is unnecessary to compress the volume of gas contained between the micropump and the external valve in order to cause said volume of gas to pass into the external valve.

Thus, for example, if the ventilation is blocked, as in the above-described situation, due to a swim in seawater, the pressure enclosed in the cavity 16 of the cover 15 is about 100 kPa or greater than 100 kPa. This pressure acts on the pressures in the liquid reservoir 6 ($P_{res}$) and in the reference chamber 5 ($P_{ref}$) of the anti-siphon valve 4, which pressures then take said value of 100 kPa. If the valves of the micropump are not sufficiently leaktight, the same pressure establishes itself at the inlet (channel 3) of the anti-siphon valve 4 ($P_{in} = 100$ kPa). When the user then travels by airplane and the airplane climbs to its cruising altitude, the pressure inside the passenger compartment of the airplane, and thus at the outlet 7 of the anti-siphon valve 4, is about 72 kPa. There is thus a pressure difference $\Delta P_{out}$ of 28 kPa between the reference chamber 5 and the outlet channel 7 of the anti-siphon valve 4. If consideration is given to the pressure $P_{in}$ in the inlet channel 3 of the valve 4 at the time the airplane climbs, if the valves of the micropump 1 are not fully leaktight, $P_{in}$ remains at the pressure value in the reference chamber 5 ($P_{ref}$), i.e. $P_{in} = P_{ref} = 100$ kPa, so that $\Delta P_{in} = 0$ (the current location is on the vertical y-axis in FIGS. 5 and 6). With a typical outlet pressure threshold $T_{out}$ of 5 kPa, the anti-siphon valve 4 does indeed remain closed.

In this way, it can be understood that the valve 4 closes again, and performs its anti-siphon function when the pressure ($P_{res}$) of the reservoir 6 is greater than the pressure of the place of injection on the patient's body, thereby preventing any leakage of liquid towards the patient that is not caused by the pump 1 operating.

It can also be understood that such an anti-siphon valve can perform its function even if it is contaminated by particles of small size because the closure remains leaktight by means of soft or pliable materials being used.

In addition, in most cases, a valve is formed that has performance as shown in the diagrams of FIGS. 5 and 6.

In which case, the anti-siphon valve presents an inlet pressure threshold $T_{in}$ of negative value and an outlet pressure threshold $T_{out}$ of positive value, so that the point O (where $\Delta P_{in} = \Delta P_{out} = 0$) is situated in the open zone: it is then said that the valve is open by default.

Thus, the valve 4 is open by default so that it therefore does not contribute to the dead volume of gas to be compressed in the liquid delivery device of the present invention. Therefore, it does not affect the self-priming performance of the pump 1.

In the second embodiment shown in FIG. 4, there is still a single piece formed by the stationary body 10/13 that comprises, side-by-side, both the housing 10 of the valve 4 and the reservoir body 13, but the seat 11a' of the valve 4 is formed at the bottom of the reservoir 6 and co-operates with a moving member 11' that is, in this embodiment, separate from the moving reservoir wall 14.

In the second embodiment, which might be said to be "nested" in shape, the film forming the moving member 11' of the valve 4 is mounted in leaktight manner on the bottom wall of the reservoir 6 so that it is said reservoir that constitutes the reference chamber 5.

A structure is thus obtained that is more compact, and equilibrium between the pressure of the reservoir $P_{res}$ and the reference pressure $P_{ref}$ is guaranteed by construction. However, operation remains the same.

For example, in the blocked-ventilation situation, the same pressure of 100 kPa is enclosed under the cover 15 and acts on the liquid in the reservoir 6 and thus also on the reference chamber 5 of the anti-siphon valve 4. If the valves of the micropump 1 are not fully leaktight, said pressure of 100 kPa then acts on the outlet pressure $P_{out}$ of the valve 4 and on the inlet pressure $P_{in}$ of the valve 4. Then, when the user is inside an airplane at its cruising altitude, the pressure in the passenger compartment of the airplane is 72 kPa. This scenario has the following consequences:

the inlet pressure $P_{in}$ of the valve 4 remains at the value of 100 kPa, so that the situation in which $P_{ref} = P_{res} = P_{in} = 100$ kPa is reached, so that $\Delta P_{in} = 0$ (location on the vertical y-axis in FIGS. 5 and 6); and the outlet pressure $P_{out}$ of the valve 4 reaches the value of 72 kPa, thereby resulting in a pressure difference $\Delta P_{out}$ of 28 kPa between the reference chamber 5 and the outlet channel 7 of the anti-siphon valve 4. With a typical outlet pressure threshold $T_{out}$ of 5 kPa, then $\Delta P_{out} > T_{out}$ and the anti-siphon valve 4 thus does indeed remain closed.

Thus, in the two embodiments shown in FIGS. 3 and 4, the external valve 4 has three ports (the inlet channel 3, the outlet channel 7, and the reference chamber 5 that is situated outside the liquid flow path). This valve 4 serves to provide safety between the pump 1 and the patient, because, in principle, it remains open and closes only in the event of a potential problem (if its outlet fluid path is at a lower pressure than the pressure outside the device).

The invention claimed is:

1. A device for delivering a liquid, which device comprises:
    a pump of a positive displacement type having an inlet valve, an outlet valve and an inlet duct suitable for being connected to an upstream liquid reservoir and connected to said inlet valve of the pump, said inlet valve of the pump being placed downstream of the inlet duct, an outlet duct connected to said outlet valve of the pump, which outlet valve is made of a rigid material,
    an anti-siphon valve external to the pump and having an inlet channel connected directly to the outlet duct of the pump, and an outlet channel, disposed between the inlet channel and the outlet channel are a seat and a moving member that co-operate together and that define, between the inlet channel and the outlet channel, a leaktight liquid flow zone, the moving member having a top surface and a bottom surface; and
    a reference chamber that is not in fluid communication with the outlet channel and having a reference pressure ($P_{ref}$), the top surface of the moving member being in contact with a fluid contained within the reference chamber having the reference pressure ($P_{ref}$),
    wherein said moving member moves from an opening position allowing the liquid to flow through said liquid flow zone, to a closure position in which the moving member comes into contact with the seat of the anti-siphon valve and prevents a flow through said liquid flow zone, when said moving member is subjected to at least said reference pressure ($P_{ref}$), wherein said reference pressure ($P_{ref}$) is substantially equal to a pressure prevailing, when the pump is at rest, in the inlet duct of the pump, and wherein the seat or the moving member of said anti-siphon valve comprises a pliable material.

2. The device according to claim 1, wherein the moving member is in the opening position when said anti-siphon valve is in an equilibrium position in which pressures in the inlet channel ($P_{in}$), in the outlet channel ($P_{out}$), and in the reference chamber ($P_{ref}$) are mutually equal;
    wherein the moving member goes into its closure position, from said equilibrium position of the anti-siphon valve, if the pressure in the outlet channel ($P_{out}$) decreases at least by a value of a predetermined outlet pressure threshold ($T_{out}$), the pressures in the inlet channel ($P_{in}$) and in the reference chamber ($P_{ref}$) remaining constant;
    and wherein the moving member goes into its closure position, from said equilibrium position of the anti-siphon valve, if the pressure in the reference chamber ($P_{ref}$) increases at least by an absolute value of a predetermined inlet pressure threshold ($T_{in}$), the pressure in the outlet channel ($P_{out}$) remaining constant.

3. The device according to claim 2, wherein said outlet channel of the anti-siphon valve is connected to an injection line, and said predetermined outlet pressure threshold ($T_{out}$) is less than an inverse of a siphon pressure ($-P_{siph}$) prevailing in the anti-siphon valve, if said injection line is disposed vertically with a distal end downwards.

4. The device according to claim 1, wherein the pump is a micropump.

5. The device according to claim 1, wherein said anti-siphon valve comprises a valve body in which said inlet channel, said liquid flow zone, and the outlet channel are formed.

6. The device according to claim 5, wherein said moving member comprises a flexible film that is fastened in a leaktight manner to a surface of the valve body, and which extends along said liquid flow zone.

7. The device according to claim 6, wherein said flexible film is made of an elastic material.

8. The device according to claim 1, wherein said reference chamber is in communication with the inlet duct of the pump.

9. The device according to claim 1, wherein the reference chamber is subjected to a pressure ($P_{ref}$) as the pressure ($P_{res}$) prevailing in the liquid reservoir.

10. The device according to claim 1, wherein said liquid reservoir has a variable volume.

11. The device according to claim 10, wherein said liquid reservoir comprises a stationary reservoir body and a moving reservoir wall defining a cavity of said liquid reservoir.

12. The device according to claim 11, wherein said moving reservoir wall is formed of a flexible film that is made of a polymer material.

13. The device according to claim 12, wherein said moving reservoir wall is made of an elastic material.

14. The device according to claim 12, wherein said anti-siphon valve comprises a valve body in which said inlet channel, said liquid flow zone, and the outlet channel are formed and wherein said moving member comprises a flexible film that is fastened in a leaktight manner to a surface of the valve body, and that extends along said liquid flow zone, and wherein said flexible film of the moving member and the flexible film of said moving reservoir wall are made as a unitary flexible film.

15. The device according to claim 14, wherein said unitary flexible film comprises a flexible first layer and a pliable second layer that is situated on a face of the unitary flexible film that faces towards the liquid reservoir and towards the seat of the anti-siphon valve.

16. The device according to claim 11, wherein said anti-siphon valve comprises a valve body in which said inlet channel, said liquid flow zone, and the outlet channel are formed and wherein said valve body and said stationary reservoir body are formed in a single piece forming a stationary body.

17. The device according to claim 16, wherein said anti-siphon valve and said liquid reservoir are defined by a same surface of said stationary body forming the valve body and the stationary reservoir body.

18. The device according to claim 17, wherein said moving reservoir wall is formed of a flexible film that is preferably made of a polymer material, wherein said moving member is formed of a flexible film that is fastened in a leaktight manner to a surface of the valve body, and that extends along said liquid flow zone, wherein said flexible film of the moving member and the flexible film of said moving reservoir wall are made as a unitary flexible film, and wherein said unitary flexible film is fastened against a same surface of the stationary body in a leaktight manner so as to form said liquid flow zone of said anti-siphon valve and the cavity of said liquid reservoir.

19. The device according to claim 18, wherein said unitary flexible film is fastened in a leaktight manner against said stationary body by an ultrasound welding, by a heat-sealing, or by a laser welding.

20. The device according to claim 18, wherein said unitary flexible film is fastened in a leaktight manner against said stationary body by an adhesive bonding.

21. The device according to claim 18, wherein said unitary flexible film is fastened in a leaktight manner against said stationary body by a precision fitting under a pressure.

22. The device according to claim 16, wherein said liquid reservoir further comprises a cover mounted on said stationary reservoir body, said moving reservoir wall being received between said cover and said stationary reservoir body, wherein said cover is mounted on said stationary body and wherein said cover and said stationary body define a space that comprises said liquid reservoir and said reference chamber.

23. The device according to claim 22, wherein said pump has a compression ratio that is higher than the ratio of the absolute opening pressures of the inlet and the outlet valves so that said pump is self-priming in the absence of the anti-siphon valve.

24. The device according to claim 23, wherein the pump has a pumping volume that is smaller than 10 µl.

25. The device according to claim 24, wherein the pump is manufactured using a micro-machining technology.

26. The device according to claim 23, wherein the pump has a pumping volume that is smaller than 1 µl.

27. The device according to claim 23, wherein the pump has a pumping volume that is smaller than 500 nl.

28. The device according to claim 11, wherein said moving reservoir wall is fastened in a leaktight manner to an outside surface of the stationary reservoir body.

29. The device according to claim 11, wherein said liquid reservoir further comprises a cover mounted on said stationary reservoir body, said moving reservoir wall being received between said cover and said stationary reservoir body.

30. The device according to claim 29, wherein said reference chamber is formed in a space defined between the cover and the moving reservoir wall.

31. The device according to claim 9, wherein the pressure ($P_{res}$) prevailing in said liquid reservoir is substantially equal to a pressure prevailing outside the liquid reservoir.

32. The device according to claim 1, wherein the liquid reservoir comprises a stationary reservoir body and a moving reservoir wall defining a cavity of the liquid reservoir, wherein the moving reservoir wall comprises a material that can deform without being elastic.

33. The device according to claim 32, the moving member and the moving reservoir wall together form a single film, wherein a reservoir portion of the single film is secured in a leaktight manner to the stationary reservoir body so that the liquid reservoir can be filled with a varying volume of a liquid without gases being present in the liquid reservoir, and wherein a valve portion of the single film is secured between the inlet channel and the outlet channel of the anti-siphon valve such that the valve portion of the single film is adapted to move between the opening position, in which liquid flows through the liquid flow zone, and the closure position, in which liquid is prevented from flowing through the liquid flow zone.

34. The device according to claim 1, wherein the bottom surface of the moving member faces the seat of the anti-siphon valve.

\* \* \* \* \*

UNITED STATES PATENT AND TRADEMARK OFFICE
CERTIFICATE OF CORRECTION

PATENT NO. : 8,167,581 B2  Page 1 of 1
APPLICATION NO. : 12/439855
DATED : May 1, 2012
INVENTOR(S) : Niklaus Schneeberger et al.

It is certified that error appears in the above-identified patent and that said Letters Patent is hereby corrected as shown below:

Column 12, Line 20, Claim 9, after "pressure" delete "($P_{ref}$) as the pressure"

Column 12, Line 57, Claim 18, after "is" delete "preferably"

Signed and Sealed this
Twenty-first Day of August, 2012

David J. Kappos
*Director of the United States Patent and Trademark Office*